United States Patent [19]
Dittrich et al.

[11] Patent Number: 5,854,072
[45] Date of Patent: Dec. 29, 1998

[54] METHOD AND APPARATUS FOR DETERMINING PRODUCT-SPECIFIC QUALITY PARAMETERS OF A LIQUID

[76] Inventors: Stephan Dittrich, Zur Tahlmühle 22, 61237 Wehrheim, Germany; Hubert Koukol, Röntgenstrasse 34, 63454 Hanau, Germany; Robert Koukol, Rückertstrasse 14, 63452 Hanau, Germany

[21] Appl. No.: 692,366

[22] Filed: Aug. 6, 1996

[30] Foreign Application Priority Data

Aug. 7, 1995 [DE] Germany .......................... 19528950.1

[51] Int. Cl.$^6$ .................................................. G01N 33/14
[52] U.S. Cl. .................... 436/24; 436/52; 436/53; 422/63; 422/82; 422/82.12
[58] Field of Search .................. 436/24, 132, 43, 436/47, 52, 53, 54; 422/63–65, 67, 81–82, 82.12

[56] References Cited

U.S. PATENT DOCUMENTS

| | | | |
|---|---|---|---|
| 3,847,551 | 11/1974 | Hutson | 23/232 R |
| 3,896,659 | 7/1975 | Goodman | 73/23.1 |
| 3,951,855 | 4/1976 | Principe et al. | 436/132 |
| 4,934,177 | 6/1990 | Cuthbertson et al. | 73/32 A |
| 4,959,228 | 9/1990 | Skrgatic et al. | 426/11 |

Primary Examiner—Lyle A. Alexander
Attorney, Agent, or Firm—Dennison, Meserole, Pollack & Scheiner

[57] ABSTRACT

The invention relates to a method and an apparatus for determining product-specific quality parameters of liquid, especially liquid (14) containing alcohol and held in a container (12) such as a bottle or can, the quality parameters being determined by means of sensors (22, 24, 26). To enable performing measurements with simply provisions and without complicated specimen preparation, and avoiding cross-sensitivities, it is proposed that the quality parameters of the liquid are determined under the conditions prevailing in the container, and liquid is initially delivered, under the pressure prevailing in the container, to a temperature unit (32) and adjusted to a temperature that corresponds to that of the sensors, and is then delivered to the sensors.

11 Claims, 1 Drawing Sheet

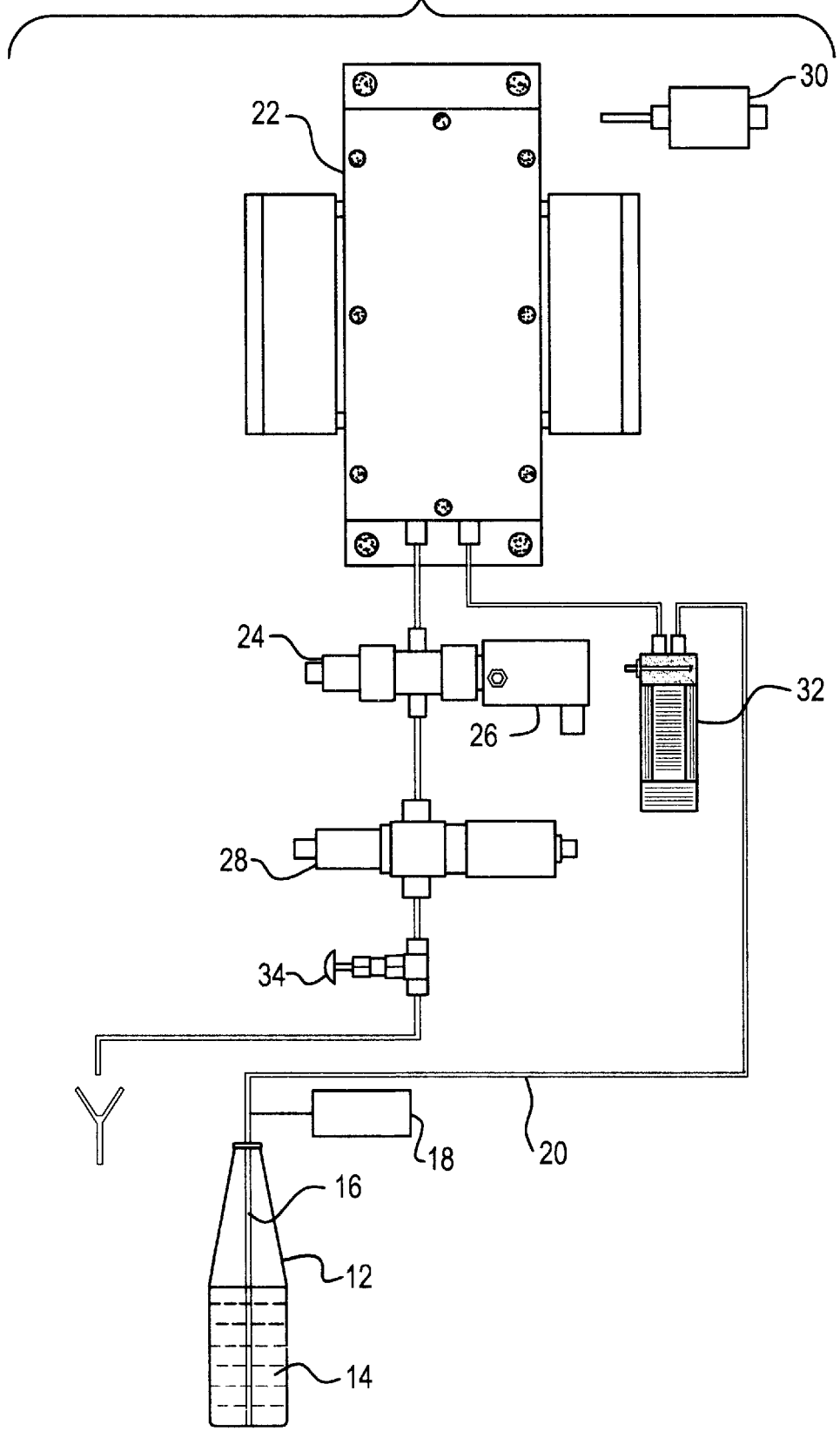

METHOD AND APPARATUS FOR DETERMINING PRODUCT-SPECIFIC QUALITY PARAMETERS OF A LIQUID

BACKGROUND OF THE INVENTION

The invention relates to a method for determining product-specific quality parameters of liquid, especially liquid containing alcohol and held in a container such as a bottle or can, the quality parameters being determined by means of sensors. The invention also relates to an apparatus for determining product-specific quality parameters of liquid, in particular containing alcohol and held in a container such as a bottle or can, by means of sensors, such as density/acoustic sensors and/or $O_2$ sensors and/or $CO_2$ sensors, and/or color sensors.

To determine the corresponding product-specific quality parameters, for instance of beer, of the prior art, complicated specimen preparations are necessary, such as removing $CO_2$ or filtration or tempering, so that certain cross-sensitivities are avoided. However, this specimen preparation often causes mistakes, such as alcohol losses in the $CO_2$ removal. Although the possibility would exist of automating the specimen preparation steps, nevertheless this would be complicated and hardly supportable in terms of cost.

SUMMARY OF THE INVENTION

The object of the present invention is to improve a method and an apparatus of the type referred to at the outset such that by simple means and without complicated specimen preparations, while and avoiding cross-sensitivities, product-specific quality parameters can be determined sufficiently accurately and replicably.

In terms of the method, the object is attained essentially in that the quality parameters of the liquid are determined under the conditions prevailing in the container, and liquid is delivered initially, under the pressure prevailing in the container, to a tempering unit, and adjusted to a temperature that corresponds to that of the sensors, and is then delivered to the sensor or sensors.

According to the invention, product-specific quality parameters are measured under the conditions prevailing in the container without prior specimen preparation, and specimen removal is done directly from the container.

For transporting the liquid, the container can be acted upon by an inert gas pressure, so that the liquid in the container continues to be under the prevailing pressure. By means of overpressure, the liquid is first delivered to the tempering unit, such as a through-flow heater, so as to adjust the liquid specimen continuously to the ambient temperature, that is, the temperature that the sensors have. The tempering of individual sensors and drift caused by temperature differences are thus avoided.

As the gas for producing an overpressure in the container, or in other words to feed the liquid to be measured through the sensors, an inner gas is used, such as nitrogen or a gas which must be free of $O_2$ or $CO_2$ when the corresponding values are to be determined. The inner gas itself should be introduced into the container at a pressure preferably between 3 and 4 bar.

The liquid itself is delivered continuously or in batches to the series-connected sensors, depending on the quality parameters to be determined. A continuous delivery is done with respect to $O_2$, $CO_2$ and color measurements, while conversely when density or alcohol content is being determined, parameter determination is done with the liquid at rest.

In order to adjust the sensors without complicated precalibration steps, it is also provided that before the quality parameters are determined, the sensors are flushed and cleaned with the tempered liquid.

It should be especially emphasized that the alcohol content of a liquid can be determined without first having to remove ingredients that influence the determination. Instead, it is merely necessary to measure the concentration of the influencing substances and then to compensate for it. As a result, the advantage is also attained that inaccuracies in alcohol determination from cross-sensitivities do not occur.

An apparatus of the type referred to at the outset is distinguished in that the container communicates with an overpressure source; that a line carrying liquid that is insertable into the container extends from the container and discharges into a tempering unit, from which the line leads to the sensors; and that the line has a pressure holding valve on its end.

It is provided in particular that the overpressure source is an inert gas overpressure source and can be made to communicate with the container via a double hollow needle insertable into the container, from which needle the line carrying liquid extends.

The sensors themselves in the line are connected in series. Moreover, the tempering unit is preferably a heater, such as a through-flow heater.

BRIEF DESCRIPTION OF THE DRAWING

The sole drawing FIGURE is a schematic diagram of an apparatus according to the invention.

DESCRIPTION OF THE PREFERRED EMBODIMENTS

In order to be able to measure product-specific quality parameters of a liquid 14, such as beer, in a container such as a bottle 10, under the conditions such as temperature and pressure prevailing in the container 12 without prior specimen preparation, the container 12 is pierced with a direct-closing mechanism with a double hollow needle 16, in such a way that the liquid 14 continues to be under the prevailing pressure. Via the double hollow needle 16, an overpressure of 3 to 4 bar, for example, is generated in the container 12 by an inert gas overpressure source 18, so that via a line 20 originating at the double hollow needle 16, the liquid 14 can be supplied to various sensors described below, by means of which product-specific quality parameters such as alcohol, sugar, $CO_2$, $O_2$, color, extinction, and pH are measured, In the line 20, a plurality of sensors are shown in series, specifically in a exemplary embodiment a density/acoustic sensor 22, an $O_2$ sensor 24, a $CO_2$ sensor 26, and a color sensor 28. In addition, a temperature sensor 30 is associated with the density/acoustic sensor 22.

In order not to have to temper the individual sensors and to avoid drift from temperature differences, the liquid flowing through the line 20 is brought, before reaching the sensors 22, 24, 26, 28, to a temperature and specifically the ambient temperature that also prevails at the sensors 22, 24, 26 and 28. To that end, the liquid first flows through a through-flow heater 32, which is incorporated into the line 20.

At the end of the line 20 is a needle valve 34, by way of which the pressure in the line 20 is kept within the requisite range. Downstream of the needle valve 34, the liquid flows out into the open.

At the onset of the measurement, first some of the liquid is heated by means of the heater 32, and then it flows through the sensors 22, 24, 26, 28 in order to flush and clean them. In addition to pretempering of the sensors 22, 24, 26 and 28, at the same time the measurement values obtained from them are called up; once constant values are attained, a second portion of the specimen liquid is delivered to the sensors 22, 24, 26, 28, so that the actual product-specific quality parameters can be determined.

If the container 12 contains beer, then the following series-connected sensors are used.

By means of the density/acoustic sensor 22, the density and the speed of sound are ascertained for original wort, alcohol and extract determination. By means of the sensors 24 and 26, $CO_2$ for carboxylic acid content and $O_2$ for oxygen content are determined. By means of the color sensor 28, which can be called a photometer, extinction and color determination are done. Finally, a pH meter is present.

The sensors 24, 26, 28, which are used for the $CO_2$ and $O_2$ extinction and color determination experience a continuous flow of the liquid specimen through them. Conversely, in the density/acoustic sensor 22, the density and speed of sound are ascertained with the liquid at rest.

With the aid of the apparatus of the invention, product-specific quality parameters, such as alcohol, sugar, $CO_2/O_2$ content, extinction and color, are determined under the conditions of the liquid 14 in the container 12, without specimen preparation; the liquid specimen is continuously preheated by the through-flow heater 32 and adjusted to the temperature of the sensors 22, 24, 26 and 28. The temperature is preferably the ambient temperature.

What is claimed is:

1. A method for determining at least one parameter of a liquid held in a closed container under pressure, comprising the steps of:

inserting into the container a gas injection line and a liquid removal line, without opening the container to atmosphere;

injecting into the container, through the gas injection line, a gas which is inert to the liquid, the injecting causing liquid to flow through the liquid removal line under pressure equivalent to the pressure in the container;

determining the temperature of a sensor for determining said at least one parameter, and adjusting the liquid in the liquid removal line to said determined temperature; and passing the liquid at said determined temperature to the sensor to determine said at least one parameter.

2. The method of claim 1, wherein the gas is nitrogen.

3. The method of claim 1, wherein the gas is injected at a pressure of about 3 to 4 bar.

4. The method of claim 1, wherein the liquid is passed to a plurality of sensors in series.

5. The method of claim 1, wherein the liquid is passed continuously or batchwise to said sensor.

6. The method of claim 1, additionally comprising flushing said sensor with a tempered liquid which is the same as the liquid in the container, before passing the liquid in the container to the sensor.

7. The method of claim 1, wherein the parameter is alcohol content.

8. An apparatus for determining at least one parameter of a liquid held in a container under pressure, comprising:

a source of gas under pressure, the gas being inert to the liquid;

means for injecting the gas under pressure into the liquid without opening the container to atmosphere;

a sensor for determining the at least one parameter which is maintained at a known temperature;

liquid removal means for removing liquid under pressure from the container without opening the container to atmosphere, the liquid removal means including a liquid removal line which is disposed between the container and the sensor;

means in association with the liquid removal line for adjusting the temperature of liquid in the liquid removal line to the known temperature; and a valve for maintaining the liquid removal line under pressure, located downstream of the sensor.

9. The apparatus of claim 8, wherein the means for injecting comprises a hollow double needle insertable into the container and presenting two connection ports, one port connected to the source of gas, the other port being connected to the liquid removal line.

10. The apparatus of claim 8, wherein a plurality of said sensors are provided in series.

11. The apparatus of claim 8, wherein the means for adjusting comprises a flow-through heater.

* * * * *